July 21, 1942. R. ENGLE Plant Pat. 534
CARNATION
Filed Jan. 12, 1942
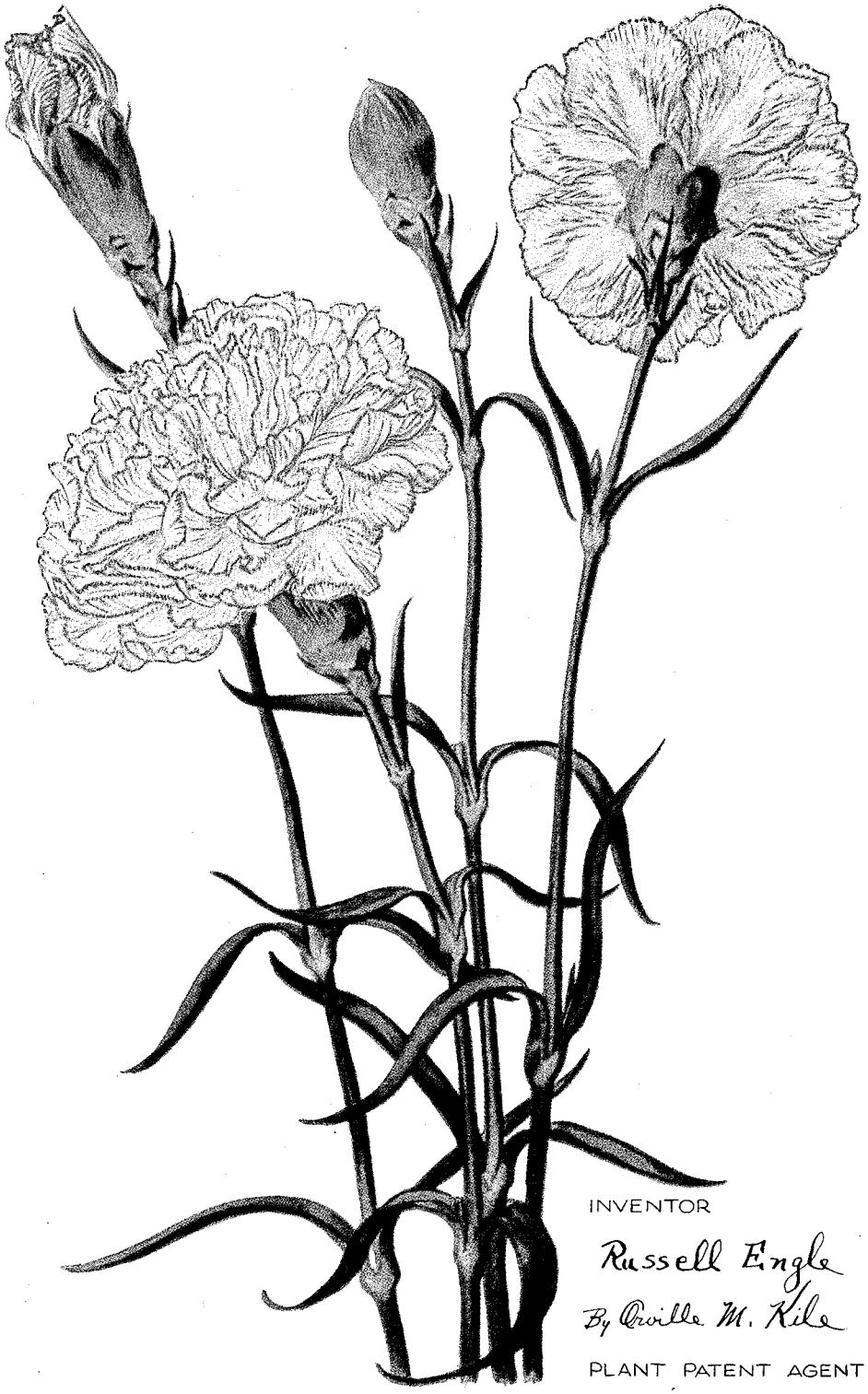
INVENTOR
Russell Engle
By Orville M. Kile
PLANT PATENT AGENT Patented July 21, 1942

UNITED STATES PATENT OFFICE

534

CARNATION

Russell Engle, Kokomo, Ind., assignor to Tom Knipe, Florist, Kokomo, Ind., a partnership Application January 12, 1942, Serial No. 426,510

1 Claim. (Cl. 47—60)

My new invention relates to improvements in carnation plants of the novelty class, with specific relation to improvements over the variety Opal which is the subject of Plant Patent No. 69. The principal improvements consist of increased strength and vigor of the plant and increased size of blossoms and stems, together with a difference in color and color placement. The Magenta splashings on the new variety are slightly darker than those of Opal and are spread over a greater portion of the petal, particularly on the reverse side of the petal.

The new variety is the result of definite breeding efforts and is not derived from Opal or its parents. It is a cross between Patrician as the female parent and an unnamed white seedling of our own as the male parent. Asexual propagation has taken place and the new plants thus produced hold the same characteristics as the original seedling.

The illustration which makes up a part of this application shows in the original a tight bud, an opening bud, a flower in front view and another showing the backs of the petals, together with portions of the stems and foliage, slightly enlarged and in approximately true colors.

Color designations in the following detailed description indicate Ridgway's Color Standards and Nomenclature.

*The plant*

Growth habit: Upright, strong and vigorous, attaining a height of about 3 feet. Roots easily and therefore propagates readily.

Blooming habit: Very free-flowering.

Disease resistance: Resistant to diseases common to carnations.

Stems: Straight and amply strong to support the heavy flowers. Attain a length of about 3 feet. Internodes relatively short, being about 2½ inches in length. Same color as foliage, except the usual lighter portion above each node.

Foliage: Ample without being grassy. Uncurled.

*Size.*—Average of lower leaves is 3¼ inches long by ¼ inch wide.

*Color.*—Between Empire Green and Dark Dull Yellow Green (Plate XXXII), covered with slight gray bloom.

*The flower*

Bud:

*Shape.*—Slender and of almost uniform thickness, with blunt end.

*Size.*—Averages 1¼ inches in length.

Bloom:

*Size.*—Medium to large, measuring from 2¾ to 3½ inches in diameter.

*Form.*—Full and very high-centered. Outer circle very regular. The inner petals are moderately crinkled and rather tightly folded and bunched but the outer petals are loosely arranged and are rather flat.

*Petalage.*—Averages about 70 petals in November.

*Fragrance.*—Mild cinnamon fragrance.

*Keeping qualities.*—Very good.

Petals:

*Color.*—White to faintly Magenta tinted with Magenta (Pl. XXVI) markings which resemble shot threads of embroidery. More of this color is seen on the backs of the petals than on the fronts. Petals are edged with a line of slightly darker color which is approximately Dull Magenta Purple (Pl. XXVI).

*Shape.*—Wedge shaped or obovate, with long shank which is inclosed in calyx. Edge is shallowly crenate.

*Size.*—Outer petals are 1½ to 1¾ inches long from calyx to tip and 1½ to 1¾ inches wide at the broadest portion, which is near the top. Entire length of petal is 2¼ to 2½ inches.

*Substance.*—Medium to heavy.

*Aspect.*—Velvety.

*Calyx.*—Consists of single tube with five lobes. Strong and seldom splits. Spinach Green (Pl. V) at top and Lettuce Green (Pl. V) at base.

*Bracts.*—Medium sized. Strong. Same color as upper part of calyx.

Reproductive organs:

*Ovary.*—Medium in size; high.

*Pistils.*—Usually 2, sometimes 3 in number; white; curled at ends; average 1¾ to 2 inches in length, usually visible beyond the petals.

*Stamens.*—Few and straggling. *Filaments*—white; varying in length and shorter than pistils. *Anthers*—white; medium in size.

*Comparison with Opal*

The known variety which is most like my new variety is Opal, the subject of Plant Patent No. 69. But there are many important and outstanding differences between these two varieties, some of which are pointed out below.

1. The strength of the entire plant of my new variety is greater than that of Opal.

2. The stems of my new variety are very much heavier, stronger, stiffer, and longer than those of Opal, the latter being thin and flaccid.

3. Buds of my new variety are longer, thicker and more bulged than those of Opal.

4. The size of the flower of my new variety is at least one-third larger than that of Opal, the former measuring 2¾ to 3½ inches across, while the latter measures only 2 to 2¼ inches across.

5. The petalage of my new variety is very much greater than that of Opal, averaging 65 petals in November as compared with 26 for Opal at the same time and grown under similar conditions.

6. There is considerably more color on the petals of the new variety, particularly on the backs of the petals, and it makes a different pattern.

7. The color markings on the petals of my new variety are darker and a little more inclined toward the purple than the markings on Opal.

8. The edge of the petals of my new variety is more shallowly serrated than those of Opal.

Having thus disclosed my invention, I claim:

The new and distinct variety of carnation plant herein shown and described, characterized particularly by its vigor and strength; its heavy, strong and upright stems; its large, blunt buds; its high-centered flowers of large size and great petalage; the unusually shallow serrations of the petals; and the distinctive dark magenta markings on the white petals, particularly on their under surface.

RUSSELL ENGLE.